United States Patent
Dasgupta et al.

(10) Patent No.: US 8,927,967 B2
(45) Date of Patent: Jan. 6, 2015

(54) ELECTROCHEMICALLY-GATED FIELD-EFFECT TRANSISTOR, METHODS FOR ITS MANUFACTURE AND USE THEREOF

(71) Applicant: Karlsruher Institut fuer Technologie, Karlsruhe (DE)

(72) Inventors: Subho Dasgupta, Eggenstein-Leopoldshafen (DE); Horst Hahn, Seeheim-Jugenheim (DE); Babak Nasr, Eggenstein-Leopoldshafen (DE)

(73) Assignee: Karlsruhe Institute of Technology, Karlsruhe (DE)

( * ) Notice: Subject to any disclaimer, the term of this patent is extended or adjusted under 35 U.S.C. 154(b) by 0 days.

(21) Appl. No.: 13/869,617

(22) Filed: Apr. 24, 2013

(65) Prior Publication Data

US 2014/0319466 A1    Oct. 30, 2014

(51) Int. Cl.
  *H01L 29/06*  (2006.01)
  *H01L 29/08*  (2006.01)
  *G01N 27/414*  (2006.01)
  *H01L 51/05*  (2006.01)

(52) U.S. Cl.
  CPC ........ *H01L 51/0562* (2013.01); *G01N 27/4146* (2013.01); *H01L 51/0558* (2013.01); *H01L 29/0669* (2013.01); *H01L 29/0665* (2013.01)
  USPC .......... 257/24; 257/14; 257/17; 257/18; 257/57; 257/288; 257/414; 257/E21.409; 257/E23.025; 257/E23.033; 257/E27.151; 257/E29.255; 361/151; 361/434; 361/500; 361/503

(58) Field of Classification Search
  CPC ........... H01L 29/0665; H01L 29/0669; H01L 51/0558; G01N 27/4146
  USPC .................. 257/14, 17, 18, 24, 57, 288, 414, 257/E21.409, E23.025, E23.033, E27.151, 257/E29.255; 361/151, 434, 500, 503
  See application file for complete search history.

(56) References Cited

U.S. PATENT DOCUMENTS

| 8,558,214 B2 * | 10/2013 | Hahn ................................ 257/9 |
| 2007/0132043 A1 * | 6/2007 | Bradley et al. ................ 257/414 |
| 2007/0138463 A1 * | 6/2007 | Herlogsson et al. ............ 257/40 |
| 2009/0039343 A1 | 2/2009 | Kugler |
| 2010/0085684 A1 * | 4/2010 | Suh et al. ...................... 361/503 |

FOREIGN PATENT DOCUMENTS

| WO | WO-2005/054869 A1 | 6/2005 |
| WO | WO-2012/025190 A1 | 3/2012 |

OTHER PUBLICATIONS

European Search Report in European Patent Application No. 12001746.2-1235, dated Jul. 18, 2012.
Giles P. Siddons et al., "Highly Efficient Gating and Doping of Carbon Nanotubes with Polymer Electrolytes," Nano Letters, (2004), vol. 4, No. 5, pp. 927-931.

(Continued)

*Primary Examiner* — Dao H Nguyen
(74) *Attorney, Agent, or Firm* — Venable LLP; Robert Kinberg; George L. Howarah

(57) ABSTRACT

An electrochemically-gated field-effect transistor includes a source electrode, a drain electrode, a gate electrode, a transistor channel and an electrolyte. The transistor channel is located between the source electrode and the drain electrode. The electrolyte completely covers the transistor channel and has a one-dimensional nanostructure and a solid polymer-based electrolyte that is employed as the electrolyte.

15 Claims, 3 Drawing Sheets

(56) References Cited

OTHER PUBLICATIONS

Taner Ozel et al., "Polymer Electrolyte Gating of Carbon Nanotube Network Transistors," Nano Letters (2005), vol. 5, No. 5, pp. 905-911.

Seung H. Ko et al., "ZnO nanowire network transistor fabrication on a polymer substrate by low-temperature, all-inorganic nanoparticle solution process," Applied Physics Letters, (2008), vol. 92, No. 15, pp. 154102.

Taekyung Lim, et al., "A nanowire-based shift register for display scan drivers", Nanotechnology 22 (2011), 405203, 7 pages.

Huixuan Liu, et al., "Transparent $SnO_2$ Nanowire Electric-Double-Layer Transistors With Different Antimony Doping Levels", IEEE Electron Device Letters, vol. 32, No. 10, Oct. 2011, pp. 1358-1360.

Huixuan Liu, et al., "Ultralow-Voltage Transparent $In_2O_3$ Nanowire Electric-Double-Layer Transistors", IEEE Electron Device Letters, vol. 32, No. 3, Mar. 2011, pp. 315-317.

Sangdan Kim, et al., "Fabrication of reliable semiconductor nanowires by controlling crystalline structure", Nanotechnology 22 (2011), 305704, 6 pages.

Sanghyun Ju, et al., "High performance ZnO nanowire field effect transistors with organic gate nanodielectrics: effects of metal contacts and ozone treatment", Nanotechnology 18 (2007) 155201, 7 pages.

Hyun Hee Park, et al., "Effect of gate dielectrics on the device performance of $SnO_2$ nanowire field effect transistors", Applied Physics Letters, 96, 102908 (2010), 4 pages.

Sanghyun Ju, et al., "Fabrication of fully transparent nanowire transistors for transparent and flexible electronics", Nature Nanotechnology, vol. 2, Jun. 2007, pp. 378-384.

W. F. Zhang, et al., "High-performance, fully transparent, and flexible zinc-doped indium oxide nanowire transistors", Applied Physics Letters, 94, 123103 (2009) 4 pages.

Sanghyun Ju, et al., "Low Operating Voltage Single ZnO Nanowire Field-Effect Transistors Enables by Self-Assembled Organic Gate Nanodielectrics", Nano Letters, Vo. 5, No. 11 (2005) pp. 2281-2286.

Daniel Kälblein, et al., "Top-Gate ZnO Nanowire Transistors and Integrated Circuits with Ultrathin Self-Assembled Monolayer Gate Dielectric", Nano Letters, (2011) 11, pp. 5309-5315.

Huixuan Liu, et al., "Ultralow-Voltage Electric Double-Layer $SnO_2$ Nanowire Transistors Gated by Microporous $SnO_2$-Based Solid Electrolyte", J. Phys. Chem. C, 2010, 114, pp. 12316-12319.

Jia Sun, et al., "Low-voltage transparent $SnO_2$ nanowire transistors gated by microporous $SiO_2$ solid-electrolyte with improved polarization response", J. Mater. Chem., 2010, 20, pp. 8010-8015.

\* cited by examiner

ELECTROCHEMICALLY-GATED FIELD-EFFECT TRANSISTOR, METHODS FOR ITS MANUFACTURE AND USE THEREOF

BACKGROUND OF THE INVENTION

1. Field of the Invention

For the purpose of explaining the development of one-dimensional nanostructure electronics, the following citations will be referenced:

The present invention relates to an electrochemically-gated field-effect transistor (FET), to methods for its manufacture, to its use, and to electronics comprising said field-effect transistor.

2. Description of the Prior Art

[1] Kim et al., "Fabrication of reliable semiconductor nanowires by controlling crystalline structure," Nanotechnology 22 (2011), 305704, 6 pages.

[2] Taekyung Lim, et al., "A nanowire-based shift register for display scan drivers," Nanotechnology 22 (2011), 405203, 7 pages.

[3] Park et al., "Effect of gate dielectrics on the device performance of $SnO_2$ nanowire field effect transistors," Applied Physics Letters, 96, 102908 (2010), 4 pages.

[4] Ju et al., "High performance ZnO nanowire field effect transistors with organic gate nanodielectrics: effects of metal contacts and ozone treatment," Nanotechnology 18 (2007) 155201, 7 pages.

[5] Zhang et al., "High-performance, fully transparent, and flexible zinc-doped indium oxide nanowire transistors," Applied Physics Letters, 94, 123103 (2009) 4 pages.

[6] Ju et al., "Low Operating Voltage Single ZnO Nanowire Field-Effect Transistors Enables by Self-Assembled Organic Gate Nanodielectrics," Nano Letters, Vo. 5, No. 11 (2005) pages 2281-2286.

[7] Ju et al., "High performance ZnO nanowire field effect transistors with organic gate nanodielectrics: effects of metal contacts and ozone treatment," Nanotechnology 18 (2007) 155201, 7 pages.

[8] Kalblein et al., "Top-Gate ZnO Nanowire Transistors and Integrated Circuits with Ultrathin Self-Assembled Monolayer Gate Dielectric," Nano Letters, (2011) 11, pages 5309-5315.

[9] Liu et al., "Ultralow-Voltage Electric Double-Layer $SnO_2$ Nanowire Transistors Gated by Microporous $SnO_2$-Based Solid Electrolyte," J. Phys. Chem. C, 2010, 114, pages 12316-12319.

[10] Sun et al., "Low-voltage transparent $SnP_2$ nanowire transistors gated by microporous $SiO_2$ solid-electrolyte with improved polarization response," J. Mater. Chem., 2010, 20, pages 8010-8015.

[11] Liu et al., "Transparent $SnO_2$ Nanowire Electric-Double-Layer Transistors With Different Antimony Doping Levels", IEEE Electron Device Letters, Vol. 32, No. 10, October 2011, pages 1358-1360.

[12] Liu et al., "Ultralow-Voltage Transparent $In_2O_3$ Nanowire Electric-Double-Layer Transistors," IEEE Electron Device Letters, Vol. 32, No. 3, March 2011, pages 315-317.

The development of one-dimensional nanostructure electronics over the last two decades has been propelled by its various applications in flexible and transparent electronic devices, including but not limited to large area displays, transparent and 'invisible' electronics, smart windows, optical and UV sensors, solar cells etc.

Single nanowire or nanowire network transistors, devices and electronics have been described for a number of applications. Generally, a combination of a $Si/SiO_2$ gate/gate oxide is used which classifies these devices as power transistors since a high-voltage source is required for their operation which, at the same time, limits their field of applications.

In contrast, low operating voltage nanowire transistors, which preferably operate at 5 V or less and are therefore compatible with batteries as well as ideal for conformable or portable electronics, have also been reported. In majority, $Al_2O_3$ is used as low leakage, high-k gate dielectric. In [1], a $SnO_2$ single-nanowire FET which uses $Al_2O_3$ as back-gate insulator is shown. Complementary devices, such as a shift register which works as a standard logic in a display scan driver, are described in [2], [3], and [4]. In [5], a similar low-voltage device with $SiN_x$ as gate insulator is reported.

In a different approach, self-assembled high-k organic dielectrics are used to build low-voltage nanowire devices. Examples include a self-assembled superlattice (SAS) as dielectric material in [6], a self-assembled nanodielectric (SAND) in [7], and transistors gated with ultra-thin self-assembled monolayers (SAMs) in [8]. These results demonstrate the possibility of manufacturing ultra-thin gate dielectrics and hence are suitable to build short-channel devices. However, these self-assembled, high-k organic dielectrics are difficult to scale up to be used in electronic devices which require production with a large throughput.

In [9-12], low-voltage operation of nanowire (either $SiO_2$ or $In_2O_3$) transistors gated by a ceramic-based solid electrolyte is described. A few micrometer thick microporous $SiO_2$ membranes are produced by plasma-enhanced chemical vapour deposition (PECVD) with $SiH_4$ and $O_2$ as reactive gases and with 100 W power and 0.2 mbar deposition pressure. In addition to the fact that the synthesis of this electrolyte is rather complex and not compatible with solution-processing routes, the microporous $SiO_2$ membranes are rigid due to their ceramic nature and therefore not compatible with applications which require flexibility, and/or bendability and/or foldability.

SUMMARY OF THE INVENTION

The main object of the present invention is therefore to provide an electrochemically-gated field-effect transistor (FET), a method for its manufacture, its use and printed electronics comprising said FET, which overcome the limitations known from the state of the art.

In particular, it is an object of the present invention to provide an electrochemically-gated FET where the drive voltages, i.e. the gate voltage and the drain voltage, are as low as 5 V or less, preferably 3 V or less.

In particular, it is a further object of the present invention to provide an electrochemically-gated FET where both the transistor channel and the gate insulator are simultaneously capable of withstanding sufficient strain so that said FET is compatible with a flexible polymer substrate.

In particular, it is a preferred object of the present invention to provide a method for manufacturing said FET through a completely solution-processed route.

In particular, it is a preferred object of the present invention to provide a method for manufacturing said FET through high-throughput techniques.

The solution of this problem is provided by an electrochemically-gated field-effect transistor (FET), by methods for its manufacture, by its use and printed electronics. Preferred features of the invention will be described in greater detail below.

The present invention is based on the concept of electrochemical-gating which allows the application of low drive voltages, thus making transistors and logic circuits battery compatible. Exceptionally good transistor characteristics of the FETs which comprise oxide nanowires as transistor channel are demonstrated here. It is suggested that these results are due to a high gating efficiency obtained with surround or three-dimensional gating offered by a solid polymer-based electrolyte as used here.

The present invention refers to an electrochemically-gated field-effect transistor, which employs
- a source electrode,
- a drain electrode,
- a gate electrode,
- a transistor channel, which is located between the source electrode and the drain electrode and is mainly built of a one-dimensional nanostructure, and
- a solid polymer-based electrolyte used as gate dielectric which covers the transistor channel completely, i.e. it involves surround or three-dimensional, gating.

The main feature of the present invention is that a high-performance FET uses one-dimensional nanostructures, preferably nanowires, nanorods, or nanowhiskers, as the transistor channel and a solid polymer-based electrolyte as the gate dielectric.

In a specially preferred embodiment, the selected one-dimensional nanostructures are oxide nanowires of ZnO, $SnO_2$, $In_2O_3$, $Ga_2O_3$, $TiO_2$, CuO, and/or $Ag_2O$.

In a further preferred embodiment, the selected one-dimensional nanostructures are oxide nanowires of doped or mixed oxides, particularly comprising
- Al and/or Sn and/or Ga doped ZnO;
- In and/or Sb (ATO) and/or Ag and/or Zn and/or F (FTO) doped $SnO_2$;
- Zn and/or Sn (ITO) and/or Ga doped $In_2O_3$;
- In and/or In and/or Zn and/or Sn doped $Ga_2O_3$;
- Co and/or C doped $TiO_2$;
- Sn and/or Zn and/or Mn and/or Fe and/or Ni and/or Co doped CuO.

In a preferred embodiment, the one-dimensional nanostructures are preferably single-crystalline.

According to the present invention, a solid polymer-based electrolyte is employed as the gate dielectric.

In a preferred embodiment, an ion-gel electrolyte and/or a solid poly-electrolyte and/or a composite solid polymer electrolyte is used as the gate dielectric. The ingredients of the composite solid polymer electrolyte preferably include but are not limited to a polymer, a plasticizer, a supporting electrolyte (salt) and a non-aqueous solvent.

In a preferred embodiment, the composite solid polymer electrolyte provided which is comprised of the following composition:
- polyvinyl alcohol (PVA), polyethylene oxide (PEO), polyvinyl chloride (PVC), poly(methyl methacrylate) (PMMA), or polyacrylonitrile (PAN), or a mixture thereof as the polymer;
- propylene carbonate (PC), ethylene carbonate (EC), dimethyl carbonate (DMC), ethylene glycol (EG), diethylene glycol (DEG), polyethylene glycol (PEG), propylene glycol (PG), or a mixture thereof as the plasticizer;
- the supporting electrolyte (salt), which is preferably non-adsorbing type and preferably possesses $K^+$, $Na^+$, $Li^+$, $H^+$, $Et_4N^+$, and $Bt_4N^+$ as a cation, where Et means ethyl and Bt means butyl, and $PF_6^-$, $ClO_4^-$ as a anion, or a mixture thereof; and
- the non-aqueous solvent which is capable of dissolving the other components; preferably dimethyl sulfoxide (DMSO), n-methyl formamide (NMF), or dimethyl formamide (DMF) or a mixture thereof.

The present invention further refers to methods of manufacturing an electrochemically-gated one-dimensional nanostructure channel FET.

According to a first embodiment of the present invention the following steps are employed which results in a so-called in-plane gate FET:
- providing a substrate on which a source electrode, a drain electrode, and a gate electrode are located, and on which a single or multiple one-dimensional nanostructure is located in a region between the source electrode and the drain electrode in such a way that it bridges the gap between the source electrode and the drain electrode, by which step a transistor channel is formed, and
- depositing a layer of a polymer-based electrolyte in such a way that it covers the transistor channel completely and the gate electrode only partially.

According to a second embodiment of the present invention the following steps are employed which results in a so-called top-gate FET:
- providing a substrate on which a source electrode and a drain electrode are located, and on which a single or multiple one-dimensional nanostructure is located in a region between the source electrode and the drain electrode in such a way that it bridges the gap between the source electrode and the drain electrode, by which step a transistor channel is formed,
- depositing a layer of a polymer-based electrolyte in such a way that it covers the transistor channel completely, and
- placing a gate electrode on top of the polymer-based electrolyte in such a way that it covers the transistor channel completely but prevents a direct contact with both the source electrode and the drain electrode.

It is explicitly noted that both embodiments include a method in which the two ends of the one-dimensional nanostructure is paced on the source electrode and the drain electrode which are already present on the substrate.

As an alternative way, both embodiments include a method in which the source electrode and the drain electrode are placed at the two ends of the one-dimensional nanostructure which is already present on the substrate.

A device according to the present invention is thus preferably obtained via a complete solution-processing route, preferably at a temperature of 200° C. or below, more preferably at room temperature, which is about 20-25° C.

Whereas solution-processable organic dielectrics, including but not limited to PMMA, PVA, or PVC, usually require high gate voltages, which result in high-power transistors, the high polarizability of a solid polymer-based electrolyte limits the drive potentials within a value of 5 V or less, preferably 3 of V or less, so that a device according to the present invention is completely battery compatible and perfectly suitable for portable electronic applications.

In addition, one-dimensional nanostructures, which preferably include nanowires, nanorods, or nanowhiskers, are usually extremely elastic. In nanowires, high elasticity is usually found to be a function of the nanowire diameter, i.e. thinner the nanowire is, higher its elasticity is. Therefore, a device according to the present invention which employs nanowires with a small diameter, preferably of 10-20 nm, should be very elastic.

The present invention further refers to printed electronics which comprises an electrochemically-gated field-effect transistor as described on any kind of flexible substrate, including paper or polymer. The obtained devices are highly flexible or bendable since both the one-dimensional nanostructures and the solid polymer-based electrolyte are capable of enduring high strain.

In addition, high transparency above 90% for the complete optical range is achieved since both the channel, which comprises a one-dimensional nanostructure, and the gate dielectric which comprises a solid polymer-based electrolyte are highly transparent.

The present invention shows a wide field of applications in high-performance transistors or logics or circuitry involving one-dimensional nanostructures as transistor channel and electrochemical-gating with solution-processable and/or printable solid polymer-based electrolytes. In addition, the present invention opens a way for use of FETs in applications involving partially or completely solution-processed and/or partially or completely printed electronic devices, transistors, RF transistors, logics, circuitry which involves such a device. Further, applications of the above mentioned device in the field of flexible and/or bendable and/or transparent and/or portable electronics and/or displays, smart packaging, smart toys, smart textiles etc. are possible. Finally, any electronics using said device which operates at a drive voltage of 5 V or less, preferably 3 V or less are provided by the present invention.

The utilization of printable dielectrics, such as a solid polymer-based electrolytes, and the use of one-dimensional nanostructures, preferably nanowires, nanorods, or nanowhiskers, result in the following advantages which are likely to appear at the same time:
- an inexpensive, high-throughput synthesis;
- a complete room-temperature processing;
- a high FET performance due to high-quality channel and high gating efficiency;
- a low operation voltage due to high capacitance (polarizability) of the dielectric, i.e. the solid polymer-based electrolyte, hence, a good candidate for battery compatible portable electronics;
- the channel and dielectric both being highly conformable and endurable to high strain can easily be fabricated on a flexible substrate for bendable, foldable, or rollable electronics,
- the nanostructures and the solid polymer-based electrolyte both being highly transparent, the device is suitable for transparent or so-called 'invisible' electronics.

Therefore, high-performance single- or multi-nanowire devices are easily obtained by using a solution-processed and/or printed polymer-based electrolyte, where the operating voltages do not exceed 5 V, preferably not exceed 3 V, thus making the device and the method for its manufacture completely battery compatible and completely solution-processable. The present invention leads to solution-processable high performance FETs.

BRIEF DESCRIPTION OF THE DRAWINGS

The present invention will be more apparent from the following description of non-limiting specific embodiments with reference to the drawings.

DETAILED DESCRIPTION OF THE INVENTION

Nanowires were prepared with a vapour liquid solid mechanism (VLS). The nanowires were placed on the substrates of the device by simply tapping the donor substrate on a receiver substrate (device substrate). Conventional e-beam lithography was used to build the devices. Using RF sputtering, tin doped indium oxide (ITO) has been deposited as electrodes on the nanowire. FET devices were made either with ZnO or $SnO_2$ nanowires, ITO electrodes were used as passive structures and an ink-jet printed highly transparent composite solid polymer-based electrolyte was used as a surround gate dielectric for the fabricated single nanowire channel transistor device.

An electrolyte was employed which consisted of the synthetic polymer poly(vinyl alcohol), PVA, the plasticizer propylene carbonate, PC, the supporting electrolyte (salt) $LiClO_4$, and the solvent dimethyl sulfoxide, DMSO.

Figure 1A:
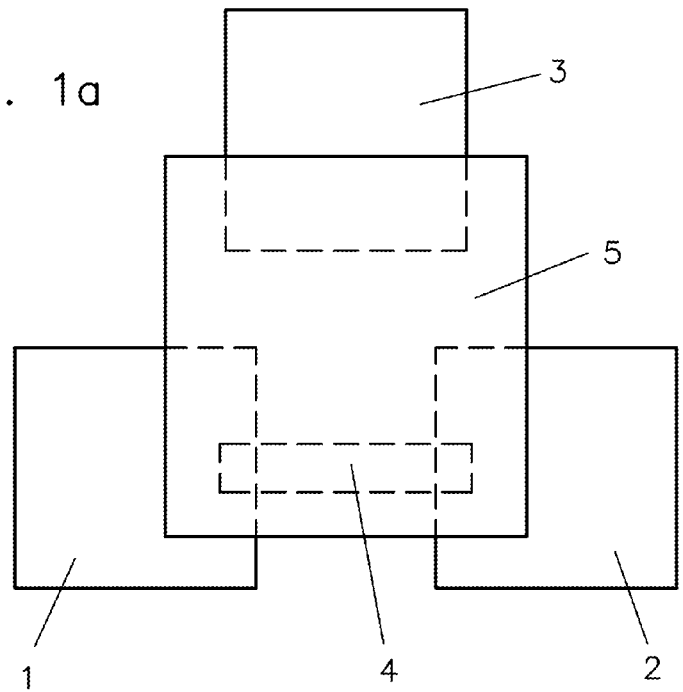
FIG. 1 shows two schemes of single-nanowire FETs according to the present invention where (a) depicts an in planegate FET and (b) a top-gate FET.
Figure 1B:
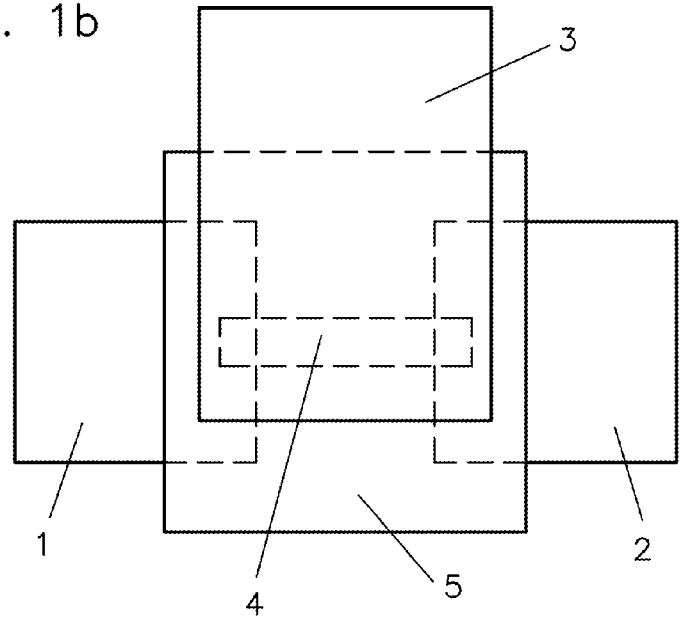

FIG. 1 shows two different schemes of single-nanowire FETs. Whereas FIG. 1a) depicts an in-plane FET, FIG. 1b) depicts a top-gate FET. In both FIG. 1a) and FIG. 1b) the electrochemically-gated FET exhibits a source electrode 1, a drain electrode 2, a gate electrode 3, a transistor channel 4, which is composed of a one-dimensional nanostructure and is located between the source electrode 1 and the drain electrode 2, and a solid polymer-based electrolyte 5 which covers the transistor channel 4 completely. In the top-gate configuration shown in FIG. 1b) the gate electrode 3 is placed on top of the solid polymer-based electrolyte 5 in such a way that it completely covers the transistor channel 4, but neither produces a direct physical contact with the source electrode 1 nor the drain electrode 2.

Figure 2A:
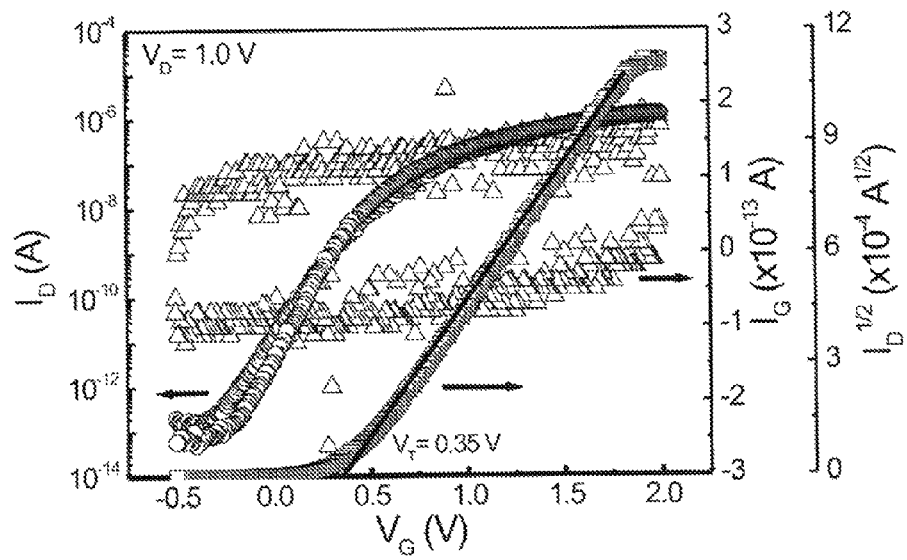
FIG. 2 displays (a) the transfer and (b) the I-V characteristics of a typical ZnO single-nanowire electrochemically-gated transistor.
Figure 2B:
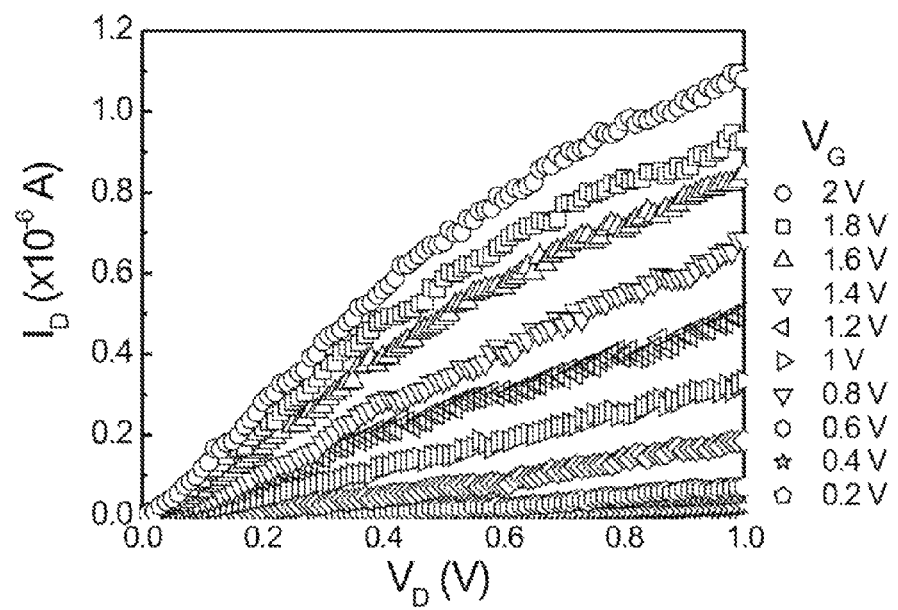

Electrical transfer characteristics were measured to evaluate the performance of the electrochemically-gated ZnO SNW-FETs. The transfer and I-V characteristic of a device are illustrated in FIG. 2a) and FIG. 2b), respectively. The device shows an excellent transistor performance with a very high On/Off current ratio of $>10^8$, a sub-threshold swing (SS) of ~117 mV/decade, a threshold voltage (VT) of only a few hundred millivolts (~350 mV), a high On-state current of more than a microampere although the nanowire radius is only 8 nm, an exceedingly high transconductance (gm) of ~82 mS/mm, and a very small gate current with a value of a fraction of a picoampere.

Most interestingly, the drive voltage (gate and drain potential) in this device is always limited to ≤2 V. The extremely low gate current and its shape as a cyclovoltammogram of a material within capacitive double layer potential window (FIG. 2a), proves that firstly, the gate current is resulting mostly from the charging of the nanowire and the electrodes connecting the nanowire, and hence it is not a real leakage current, and secondly the very small value of the gate current undoubtedly confirms an excellent insulating property of the solid polymer-based electrolyte.

As a result, the electrochemical-gating concept can principally be compared to the dielectric gating as it is shown here that electrochemical-gating involves only electrostatic field and charging and no chemical adsorptions or redox reactions at the nanowire/electrolyte interface.

The operation mechanism of such a device can be understood as follows. The switching of the transistor is controlled with the accumulated surface charge, commonly referred to electric charge double layer (ECDL) which is formed at the nanowire/electrode and electrolyte interface. At a negative gate voltage, the channel is positively charged; therefore, the FET channel, made of ZnO, an electron conductor, is at the Off-state. At zero gate bias, i.e. close to zero charge at the nanowire surface, the transistor is still 'Off' as there are not enough intrinsic carriers to cause a large channel conductance. Finally, the positive gate bias attracts positive ions toward the channel surface which in turn leads to electron accumulation in the channel and leads to an On-state of the transistor. Thus the FET can be considered as a normally-Off, accumulation-mode, n-channel MOSFET (NMOS).

Figure 3A:
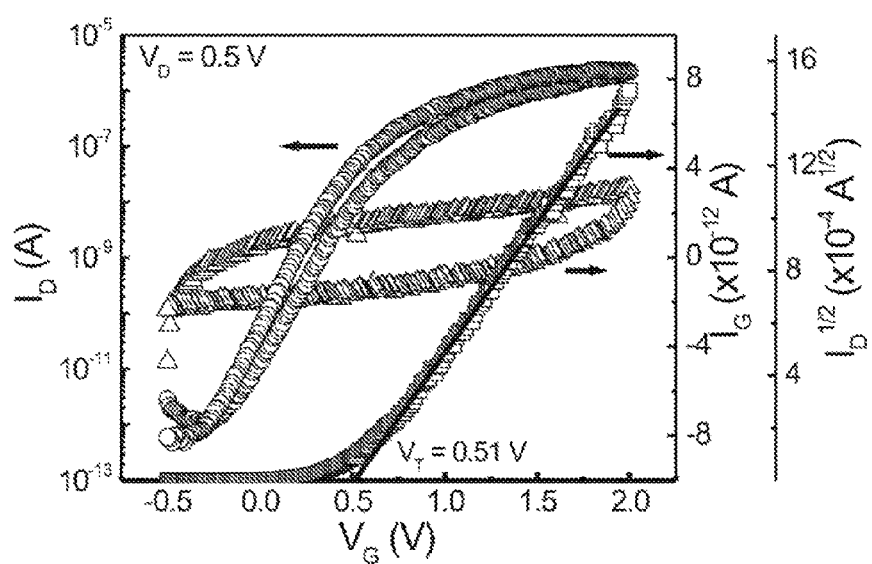
FIG. 3 displays (a) the transfer and (b) the I-V characteristics of a typical $SnO_2$ single-nanowire electrochemically-gated transistor.
Figure 3B:
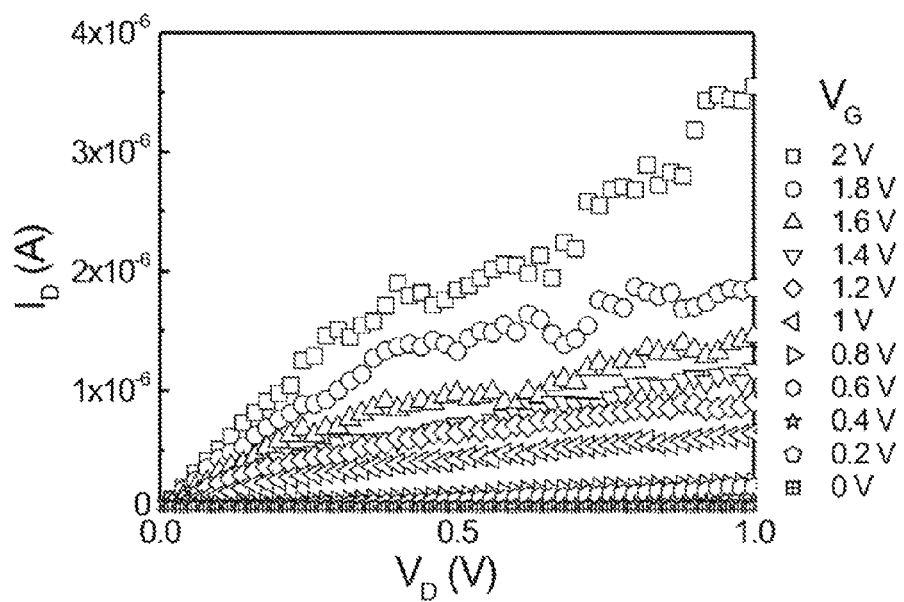

$SnO_2$ SNW-FETs were prepared following an exactly similar method as for ZnO SNW-FETs. The transfer and I-V characteristics are shown in FIG. 3a) and FIG. 3b), respectively. Transfer characteristic shows excellent operating feature with high current On/Off ratio of ~$10^7$, a very low sub-threshold swing (SS) of only ~147 mV/decade, threshold voltage (VT) of ~0.51 V, an On-state current of ~2.2 μA and a transconductance (gm) of 145 μS/mm. The operating voltage in this case is also limited to 2 V.

When solution processed, it is interesting to put such devices on extremely inexpensive substrates, preferably polymer, or paper, to further reduce the production costs. However, such a flexible substrate requires that the complete device is conformable, in fact, such bendablity, foldability, rollability add a further merit to these devices as it would open up additional applications.

For this reason, it is essential to use a solid polymer-based electrolyte as the gate dielectric and the ultra-thin nanowires as the channel of the FETs. The thin nanowires can accommodate really large elastic strain without introducing any plastic-deformation/dislocations. In transmission electron microscopy (TEM) and high resolution transmission electron microscopy (HRTEM) images of bent ZnO and $SnO_2$ nanowires it can be seen that each of them can exhibit a really small bending radius, however, the complete strain can be attributed to elastic lattice deformation as no plastic lattice distortion or presence of dislocation is observed in HRTEM or Fourier transformed HRTEM images. This high elasticity of the thin nanowires ensures that FETs made from these one-dimensional nanostructures along with a solid polymer-based electrolyte as the gate dielectric will be extremely suitable for flexible substrate and for application as bendable, flexible electronics.

Both high performance ZnO nanowire and $SnO_2$ nanowire FET devices were manufactured, which proves that the method works generally and is at least applicable to all FETs where the transistor channel is made of one-dimensional nanostructures of oxide semiconductors.

The invention claimed is:

1. Electrochemically-gated field-effect transistor, comprising:
   a source electrode,
   a drain electrode,
   a gate electrode,
   a transistor channel, which is located between the source electrode and the drain electrode, and
   an electrolyte, which covers the transistor channel completely,
   characterized in that the transistor channel comprises a one-dimensional oxide nanostructure and a solid polymer-based electrolyte is employed as the electrolyte.

2. Electrochemically-gated field-effect transistor according to claim 1, characterized in that the one-dimensional nanostructure comprises a nanowire, a nanorod, or a nanowhisker.

3. Electrochemically-gated field-effect transistor according to claim 2, characterized in that the nanowire comprises an oxide nanowire of ZnO, $SnO_2$, $In_2O_3$, $Ga_2O_3$ $TiO_2$, CuO, and/or $Ag_2O$, or of a doped or mixed oxide, including Al and/or Sn and/or Ga doped ZnO; In and/or Sb and/or Ag and/or Zn and/or F doped $SnO_2$; Zn and/or Sn and/or Ga doped $In_2O_3$; In and/or In and/or Zn and/or Sn doped $Ga_2O_3$; Co and/or C doped $TiO_2$, Sn and/or Zn and/or Mn and/or Fe and/or Ni and/or Co doped CuO.

4. Electrochemically-gated field-effect transistor according to claim 1, characterized in that the solid polymer-based electrolyte comprises an ion-gel electrolyte or a solid poly-electrolyte or a composite solid polymer electrolyte.

5. Electrochemically-gated field-effect transistor according to claim 4, characterized in that the composite solid polymer electrolyte comprises a synthetic polymer, a plasticizer, a supporting electrolyte, and a solvent.

6. Method of manufacturing an electrochemically-gated field effect transistor according to claim 1, such method comprising the following steps:
   providing a substrate on which a source electrode, a drain electrode, and a gate electrode are located, and on which a single or multiple one-dimensional nanostructure is located in a region between the source electrode and the drain electrode in such a way that it bridges the gap between the source electrode and the drain electrode, by which step a transistor channel is formed, and
   depositing a layer of a polymer-based electrolyte in such a way that it covers the transistor channel completely and the gate electrode partially.

7. Method according to claim 6, where a nanowire, a nanorod, or a nanowhisker is used as the one-dimensional nanostructure.

8. Method according to claim 7, where the one-dimensional nanostructure comprises an oxide nanowire of ZnO, $SnO_2$, $In_2O_3$ $TiO_2$, CuO, $Ag_2O$, or is a doped or mixed oxide nanowire, which include Al and/or Sn and/or Ga doped ZnO; In and/or Sb and/or Ag and/or Zn and/or F doped $SnO_2$; Zn and/or Sn and/or Ga doped $In_2O_3$; In and/or In and/or Zn and/or Sn doped $Ga_2O_3$; Co and/or C doped $TiO_2$; Sn and/or Zn and/or Mn and/or Fe and/or Ni and/or Co doped CuO is applied.

9. Method according to claim 6, where a layer of an ion-gel electrolyte or of a solid poly-electrolyte or of a composite solid polymer electrolyte is used as the electrolyte.

10. Method according to claim 9, where a composition which includes a synthetic polymer, a plasticizer, a supporting electrolyte, and a solvent is used as the composite solid polymer electrolyte.

11. Method according to claim 6, where a processing temperature of 200° C. or below is applied.

12. Use of an electrochemically-gated field-effect transistor according to claim 11 in printed electronic devices, radio frequency transistors, logics, circuits, transparent and flexible displays etc.

13. Method of manufacturing an electrochemically-gated field-effect transistor according to claim 1, such method comprising the following steps:
   providing a substrate on which a source electrode and a drain electrode are located, and on which a single or multiple one-dimensional nanostructure is located in a region between the source electrode and the drain electrode in such a way that it bridges the gap between the source electrode and the drain electrode, by which step a transistor channel is formed,
   depositing a layer of a polymer-based electrolyte in such a way that it covers the transistor channel completely, and
   placing a gate electrode on top of the polymer-based electrolyte in such a way that it covers the transistor channel completely but prevents a direct contact with both the source electrode and the drain electrode.

14. Use of an electrochemically-gated field-effect transistor according to claim 1 in flexible and/or bendable and/or transparent and/or printed electronics with an operating voltage of 5 V or less.

15. Electronics comprising an electrochemically-gated field-effect transistor according to claim 1.

* * * * *